(12) United States Patent
Schallner et al.

(10) Patent No.: US 6,559,102 B1
(45) Date of Patent: May 6, 2003

(54) SUBSTITUTED 3-ARYL-PYRAZOLES

(75) Inventors: Otto Schallner, Monheim (DE); Karl-Heinz Linker, Leverkusen (DE); Joachim Kluth, Langenfeld (DE); Mark Wilhelm Drewes, Langenfeld (DE); Dieter Feucht, Monheim (DE); Rolf Pontzen, Leichlingen (DE); Ingo Wetcholowsky, Cond. Estancia Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/279,669

(22) Filed: Oct. 24, 2002

Related U.S. Application Data

(62) Division of application No. 09/763,429, filed as application No. PCT/EP99/05963 on Feb. 26, 2001, now Pat. No. 6,495,492.

(30) Foreign Application Priority Data

Aug. 26, 1998 (DE) .......................................... 198 38 706

(51) Int. Cl.⁷ .................... C07D 231/12; C07D 231/16; A61K 31/415; A01N 43/56
(52) U.S. Cl. ..................... 504/280; 548/375.1; 514/406
(58) Field of Search ....................... 548/375.1; 504/280; 514/406

(56) References Cited

U.S. PATENT DOCUMENTS

| | | | |
|---|---|---|---|
| 5,032,165 A | 7/1991 | Miura et al. | |
| 5,112,384 A | 5/1992 | Miura et al. | |
| 5,281,571 A | 1/1994 | Woodard et al. | ............. 504/225 |
| 5,466,662 A | 11/1995 | Singhbansal et al. | |
| 6,121,201 A | 9/2000 | Pulman et al. | ............... 504/230 |
| 6,303,543 B1 | 10/2001 | Pulman et al. | ............... 504/242 |
| 6,333,296 B1 | 12/2001 | Pulman et al. | |

FOREIGN PATENT DOCUMENTS

| | | |
|---|---|---|
| EP | 0 135 833 | 4/1985 |
| EP | 0 822 187 | 2/1998 |
| WO | 92/02509 | 2/1992 |
| WO | 92/06962 | 4/1992 |
| WO | 95/33728 | 12/1995 |
| WO | 97/40018 | 10/1997 |
| WO | 97/46535 | 12/1997 |

*Primary Examiner*—Alan L. Rotman
*Assistant Examiner*—Rebecca Anderson
(74) *Attorney, Agent, or Firm*—Richard E. L Henderson; Raymond J. Harmuth

(57) ABSTRACT

The invention relates to novel substituted 3-aryl-pyrazoles of the general formula (I)

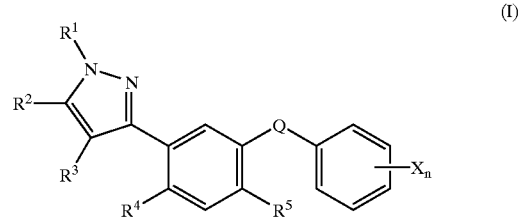

in which n, Q, $R^1$, $R^2$, $R^3$, $R^4$, $R^5$ and X are each as defined in the description, and also to processes for their preparation and to their use as herbicides.

18 Claims, No Drawings

SUBSTITUTED 3-ARYL-PYRAZOLES

This application is a divisional application of U.S. patent application Ser. No. 09/763,429 filed Feb. 20, 2001 and now U.S. Pat. No. 6,495,492, Notice of Allowance Issued Aug. 9, 2002, which in turn was the national stage of PCT/EP99/05963 filed Feb. 26, 2001, which in turn claimed priority of German Patent DE 198 38 706.7, filed Aug. 26, 1998.

FIELD OF THE INVENTION

The invention relates to novel substituted 3-aryl-pyrazoles, to processes for their preparation and to their use as herbicides.

BACKGROUND OF THE INVENTION

It is known that certain substituted 3-aryl-pyrazoles have herbicidal properties (cf. EP-A-361114, EP-A-447055, WO-A-92/02509, WO-A-92/06962, WO-A-94/26109, WO-A-95/33728, WO-A-97/40018, WO-A-97/46535). However, the herbicidal activity of these compounds and their compatibility with crop plants are not always entirely satisfactory.

SUMMARY OF THE INVENTION

Substituted 3-aryl-pyrazoles have the general formula (I)

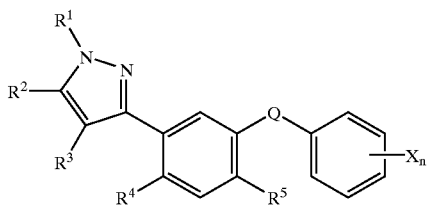

(I)

n, Q, $R^1$, $R^2$, $R^3$, $R^4$, $R^5$, and X are as described.

DETAILED DESCRIPTION

This invention, accordingly, provides the novel substituted 3-aryl-pyrazoles of the general formula (I)

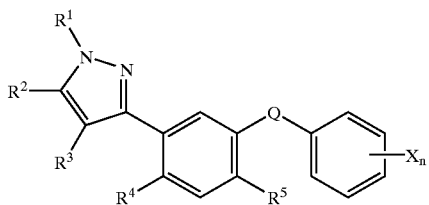

(I)

in which
n represents the numbers 0, 1, 2, 3, 4 or 5,
Q represents O (oxygen), S (sulphur), SO, $SO_2$, NH or $N(C_1-C_4$-alkyl),
$R^1$ represents hydrogen, represents optionally cyano-, halogen- or $C_1-C_4$-alkoxy-substituted alkyl having 1 to 6 carbon atoms, represents in each case optionally halogen-substituted alkenyl or alkinyl having in each case 2 to 6 carbon atoms, or represents in each case optionally cyano-, halogen- or $C_1-C_4$-alkyl-substituted cycloalkyl or cycloalkylalkyl having in each case 3 to 6 carton atoms in the cycloalkyl group and optionally 1 to 4 carbon atoms in the alkyl moiety, $R^2$ represents in each case optionally cyano-, halogen-, $C_1-C_4$-alkoxy-, $C_1-C_4$-alkylthio-, $C_1-C_4$-alkylsulphinyl- or $C_1-C_4$-alkylsulphonyl-substituted alkyl, alkoxy, alkylthio, alkylsulphinyl or alkylsulphonyl having in each case 1 to 6 carbon atoms, represents in each case optionally halogen-substituted alkenyl, alkenyloxy, alkenylthio, alkinyl, alkinyloxy or alkinylthio having in each case 2 to 6 carbon atoms, or represents in each case optionally cyano-, halogen- or $C_1-C_4$-alkyl-substituted cycloalkyl or cycloalkylalkyl having in each case 3 to 6 carbon atoms in the cycloalkyl group and optionally 1 to 4 carbon atoms in the alkyl moiety, $R^3$ represents hydrogen, halogen or optionally cyano-, halogen-, $C_1-C_4$-alkoxy-, $C_1-C_4$-alkylthio-, $C_1-C_4$-alkylsulphinyl- or $C_1-C_4$-alkylsulphonyl-substituted alkyl having 1 to 6 carbon atoms, $R^4$ represents hydrogen, cyano, thiocarbamoyl or halogen, $R^5$ represents cyano, thiocarbamoyl, halogen, or represents in each case optionally halogen-substituted alkyl, alkoxy, alkylthio, alkylsulphinyl or alkylsulphonyl having in each case 1 to 6 carbon atoms, and X represents hydroxyl, amino, nitro, cyano, carboxyl, carbamoyl, thiocarbamoyl, fluorine, chlorine, bromine, iodine, represents in each case optionally hydroxyl-, cyano-, carboxyl-, carbamoyl-, fluorine-, chlorine-, $C_1-C_4$-alkoxy-, $C_1-C_4$-alkylthio-, $C_1-C_4$-alkylsulphinyl-, $C_1-C_4$-alkylsulphonyl-, $C_1-C_4$-alkylcarbonyl-, $C_1-C_4$-alkoxy-carbonyl-, $C_1-C_4$-alkylamino-carbonyl- or di-($C_1-C_4$-alkyl)-amino-carbonyl-substituted alkyl, alkoxy, alkylthio, alkylsulphinyl, alkylsulphonyl or alkylamino having in each case 1 to 6 carbon atoms, represents dialkylamino having in each case 1 to 6 carbon atoms in the alkyl groups, represents in each case optionally cyano-, fluorine-, chlorine-, bromine- or $C_1-C_4$-alkoxy-substituted, alkylcarbonyl, alkoxycarbonyl or alkylaminocarbonyl having in each case 1 to 6 carbon atoms in the alkyl groups, represents dialkylaminocarbonyl having 1 to 6 carbon atoms in the alkyl groups, or represents in each case optionally cyano-, carboxyl-, carbamoyl-, fluorine-, chlorine-, bromine-, $C_1-C_4$-alkoxy-carbonyl-, $C_1-C_4$-alkylamino-carbonyl- or di-($C_1-C_4$-alkyl)-amino-carbonyl-substituted alkylcarbonylamino, alkoxycarbonylamino, alkylsulphonylamino, alkenyl, alkenyloxy, alkenyloxycarbonyl, alkinyl, alkinyloxy or alkinyloxycarbonyl having in each case up to 6 carbon atoms, except for the previously known compounds 4-chloro-3-[4-chloro-2-fluoro-5-(4-nitro-phenoxy)-phenyl]-1-methyl-5-trifluoromethyl-1H-pyrazole, 4-chloro-3-[4-chloro-2-fluoro-5-(4-trifluoromethyl-phenoxy)-phenyl]-1-methyl-5-trifluoromethyl-1H-pyrazole, 4-chloro-3-[4-chloro-2-fluoro-5-(2-nitro-4-trifluoromethyl-phenoxy)-phenyl]-1-methyl-5-trifluoromethyl-1H-pyrazole and 4-chloro-3-[4-chloro-2-fluoro-5-(2-chloro-4-trifluoromethyl-phenoxy)-phenyl]-1-methyl-5-trifluoromethyl-1H-pyrazole (cf. WO-A-92/06962 and U.S. Pat. No. 5,281,571).

In the definition, the hydrocarbon chains, such as alkyl, are in each case straight-chain or branched—including in combination with heteroatoms, such as in alkoxy.

Preferred substituents of the radicals listed in the formula (I) shown above are explained below:

n preferably represents the numbers 0, 1, 2 or 3.

Q preferably represents O (oxygen), S (sulphur), SO, $SO_2$, NH or $N(CH_3)$.

$R^1$ preferably represents hydrogen, represents in each case optionally cyano-, fluorine-, chlorine-, methoxy- or ethoxy-substituted methyl, ethyl, n- or i-propyl, n-, i-, s- or t-butyl, represents in each case optionally fluorine-, chlorine- and/or bromine-substituted propenyl, butenyl, propinyl or butinyl, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl.

$R^2$ preferably represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents in each case optionally fluorine-, chlorine- and/or bromine-substituted propenyl, butenyl, propenyloxy, butenyloxy, propenylthio, butenylthio, propinyl, butinyl, propinyloxy, butinyloxy, propinylthio or butinylthio, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl.

$R^3$ preferably represents hydrogen, fluorine, chlorine, bromine, or represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulfonyl-, n- or i-propylsulphonyl-substituted methyl, ethyl, n- or i-propyl.

$R^4$ preferably represents hydrogen, cyano, thiocarbamoyl, fluorine, chlorine or bromine.

$R^5$ preferably represents cyano, thiocarbamoyl, fluorine, chlorine, bromine, or represents in each case optionally fluorine- and/or chlorine-substituted methyl, ethyl, methoxy, ethoxy, methylthio, ethylthio, methylsulphinyl, ethylsulphinyl, methylsulphonyl or ethylsulphonyl.

X preferably represents hydroxyl, amino, nitro, cyano, carboxyl, carbamoyl, thiocarbamoyl, fluorine, chlorine, bromine, iodine, represents in each case optionally hydroxyl-, cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethylaminocarbonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, represents dimethylamino or diethylamino, represents in each case optionally cyano-, fluorine-, chlorine-, bromine-, methoxy- or ethoxy-substituted acetyl, propionyl, n- or i-butyroyl, methoxycarbonyl, ethoxycarbonyl, methylaminocarbonyl or ethylamino-carbonyl, represents dimethylaminocarbonyl or diethylaminocarbonyl, or represents in each case optionally cyano-, carboxyl-, carbamoyl-, fluorine-, chlorine-, bromine-, methoxycarbonyl-, ethoxycarbonyl-, methylaminocarbonyl-, ethylaminocarbonyl- or dimethylaminocarbonyl-substituted acetylamino, propionylamino, n- or i-butyroylamino, methoxycarbonylamino, ethoxycarbonylamino, methylsulphonylamino, ethylsulphonylamino, n- or i-propylsulphonylamino, n-, i-, s- or t-butylsulphonylamino, ethenyl, propenyl, butenyl, represents propenyloxy, butenyloxy, propenyloxycarbonyl, butenyloxycarbonyl, ethinyl, propinyl, butinyl, propinyloxy, butinyloxy, propinyloxycarbonyl or butinyloxycarbonyl.

n particularly preferably represents the numbers 1 or 2.

Q particularly preferably represents O (oxygen) or S (sulphur).

$R^1$ particularly preferably represents hydrogen or represents in each case optionally fluorine- and/or chlorine-substituted methyl or ethyl.

$R^2$ particularly preferably represents in each case optionally fluorine- and/or chlorine-substituted methyl, ethyl, methoxy, ethoxy, methylthio, ethylthio, methylsulphinyl, ethylsulphinyl, methylsulphonyl or ethylsulphonyl.

$R^3$ particularly preferably represents hydrogen, chlorine or bromine.

$R^4$ particularly preferably represents hydrogen, fluorine or chlorine.

$R^5$ particularly preferably represents cyano, thiocarbamoyl, chlorine, bromine, methyl or trifluoromethyl.

X particularly preferably represents nitro, chlorine or fluorine represents in each case optionally cyano-, carboxyl-, carbamoyl-, fluorine-, chlorine-, methoxy-, ethoxy-, n- or i-propoxy-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethylamino-carbonyl-substituted methyl, ethyl, methoxy, ethoxy or ethenyl.

Q very particularly preferably represents O (oxygen).

$R^5$ very particularly preferably represents cyano, thiocarbamoyl or trifluoromethyl.

$R^5$ most preferably represents cyano.

Preference according to the invention is given to those compounds of the formula (I) which contain a combination of the meanings given above as being preferred.

Particular preference according to the invention is given to those compounds of the formula (I) which contain a combination of the meanings given above as being particularly preferred.

Very particular preference according to the invention is given to those compounds of the formula (I) which contain a combination of the meanings given above as being very particularly preferred.

A further very particularly preferred group are the compounds of the general formula (IA)

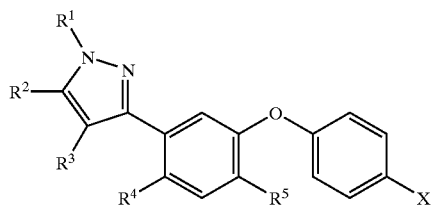

(IA)

in which

R¹ represents methyl,

R² represents methyl, trifluoromethyl, methoxy, difluoromethoxy, methylthio, methylsulphinyl or methylsulphonyl, R³ represents hydrogen, chlorine or bromine, R⁴ represents hydrogen, fluorine or chlorine, R⁵ represents cyano or thiocarbamoyl, and X represents in each case optionally cyano-, carboxyl-, carbamoyl-, fluorine-, chlorine-, methoxy-, ethoxy-, n- or i-propoxy-, methoxycarbonyl-, ethoxy-carbonyl-, n- or i-propoxy-carbonyl-, methylaminocarbonyl-, ethylamino-carbonyl-, n- or i-propylamino-carbonyl-, dimethylaminocarbonyl- or diethylaminocarbonyl-substituted methyl, ethyl, methoxy, ethoxy or ethenyl.

A further very particularly preferred group are the compounds of the general formula (IB)

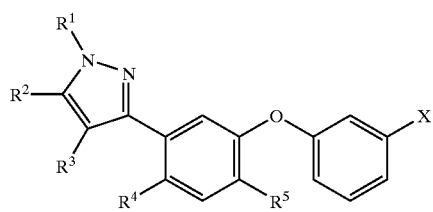

(IB)

in which

R¹, R², R³, R⁴, R⁵ and X are each as defined above.

The abovementioned general or preferred radical definitions apply both to the end products of the formula (I) and, correspondingly, to the starting materials or intermediates required in each case for the preparation. These radical definitions can be combined with each other at will, i.e. including combinations between the given preferred ranges.

Examples of the compounds of the general formula (I) according to the invention are listed in the groups below.

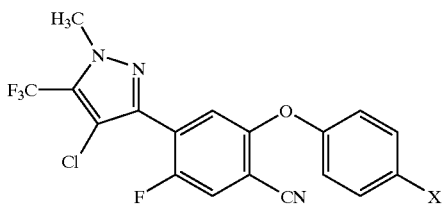

Group 1

Here, X has the meanings given in the list below:

carboxymethyl, methoxycarbonylmethyl, ethoxycarbonylmethyl, n- and i-propoxy-carbonylmethyl, carboxyethyl, methoxycarbonylethyl, ethoxycarbonylethyl, n- and i-propoxycarbonylethyl, carboxymethoxy, methoxycarbonylmethoxy, ethoxycarbonylmethoxy, n- and i-propoxycarbonylmethoxy, 1-carboxy-ethoxy, 1-methoxycarbonyl-ethoxy, 1-ethoxycarbonyl-ethoxy, 1-(n-propoxycarbonyl)-ethoxy, 1-(i-propoxy-carbonyl)-ethoxy, 2-carboxyethenyl, 2-methoxycarbonyl-ethenyl, 2-ethoxycarbonyl-ethenyl, 2-(n-propoxycarbonyl)-ethenyl, 2-(i-propoxycarbonyl)-ethenyl.

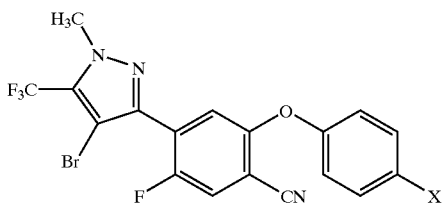

Group 2

Here, X has the meanings given above in Group 1.

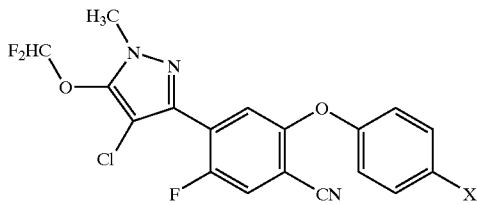

Group 3

Here, X has the meanings given above in Group 1.

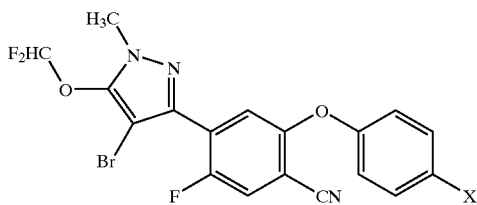

Group 4

Here, X has the meanings given above in Group 1.

Group 5

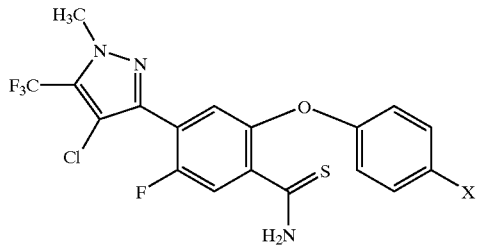

Here, X has the meanings given above in Group 1.

Group 6

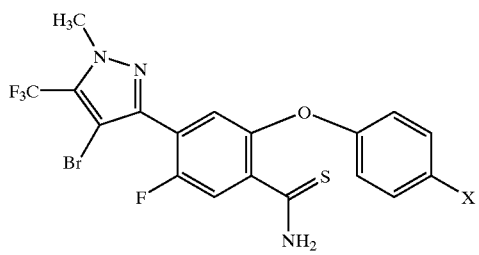

Here, X has the meanings given above in Group 1.

Group 7

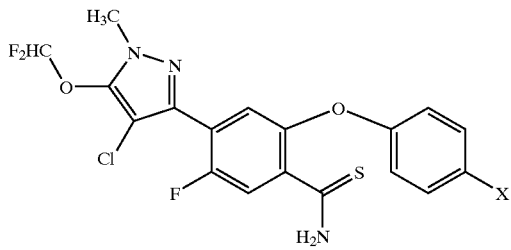

Here, X has the meanings given above in Group 1.

Group 8

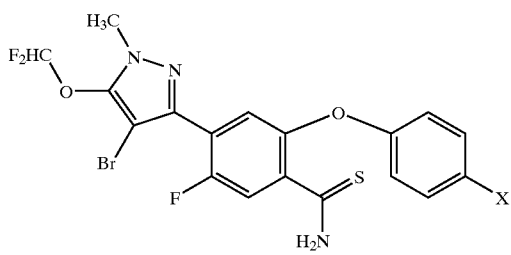

Here, X has the meanings given above in Group 1.

Group 9

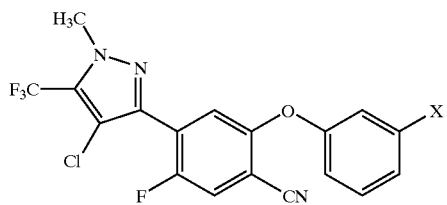

Here, X has the meanings given above in Group 1.

Group 10

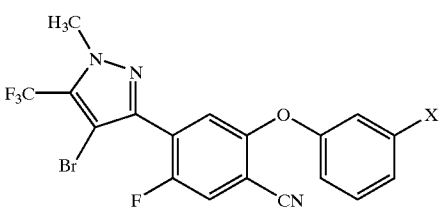

Here, X has the meanings given above in Group 1.

Group 11

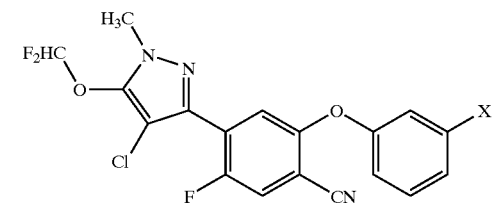

Here, X has the meanings given above in Group 1.

Group 12

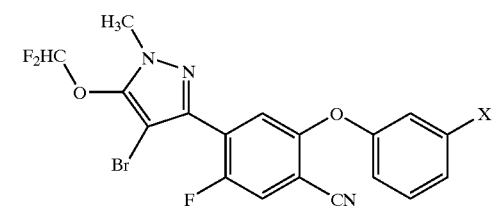

Here, X has the meanings given above in Group 1.

Group 13

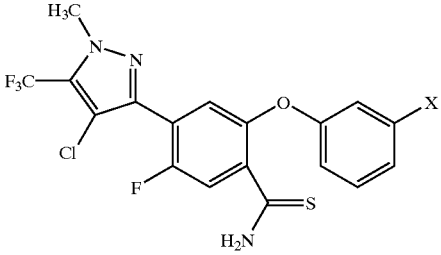

Here, X has the meanings given above in Group 1.

Group 14

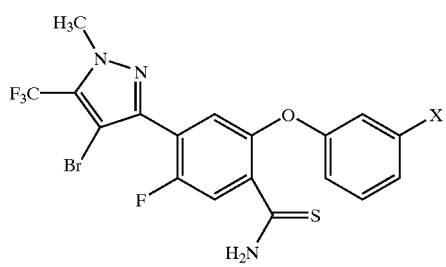

Here, X has the meanings given above in Group 1.

Group 15

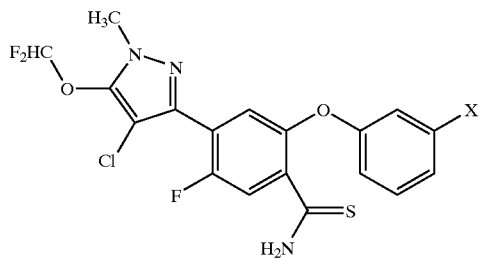

Here, X has the meanings given above in Group 1.

Group 16

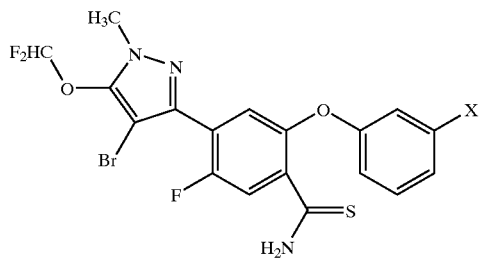

Here, X has the meanings given above in Group 1.

The novel substituted 3-aryl-pyrazoles of the general formula (I) have interesting biological properties. In particular, they have strong herbicidal activity.

The novel substituted 3-aryl-pyrazoles of the general formula (I) are obtained when (a) 3-halogenophenyl-pyrazoles of the general formula (II)

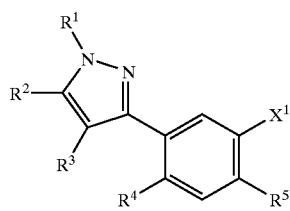
(II)

in which
$R^1$, $R^2$, $R^3$ and $R^4$ are each as defined above and
$X^1$ represents halogen
are reacted with aryl compounds of the general formula (III)

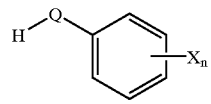
(III)

in which
n, Q and X are each as defined above
or with metal salts of compounds of the general formula (III),
if appropriate in the presence of a reaction auxiliary and if appropriate in the presence of a diluent, or when (b) substituted 3-phenyl-pyrazoles of the general formula (IV)

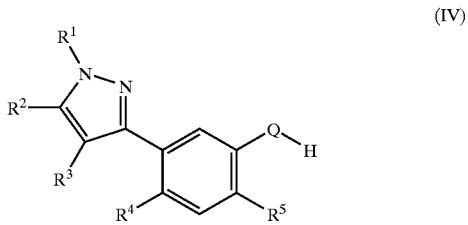
(IV)

in which
Q, $R^1$, $R^2$, $R^3$ and $R^4$ are each as defined above
or metal salts of compounds of the general formula (IV) are reacted with diaryliodonium compounds of the general formula (V)

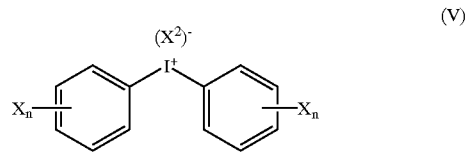
(V)

in which
n and X are as defined above and
$X^2$ represents halogen,
if appropriate in the presence of a reaction auxiliary and if appropriate in the presence of a diluent.

Using, for example, 4-chloro-3-(4-cyano-2,5-difluorophenyl)-5-difluoromethoxy-1-methyl-1H-pyrazole and methyl 2-mercapto-benzoate as starting materials, the course of the reaction in the process (a) according to the invention can be illustrated by the following equation:

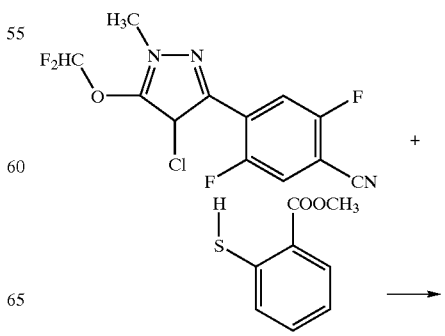

-continued

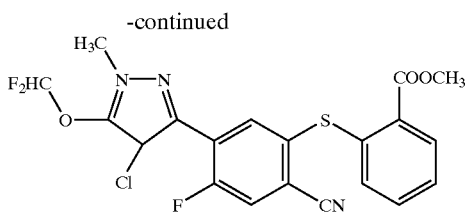

Using, for example, 4-bromo-3-(4-cyano-2-fluoro-5-hydroxy-phenyl)-1-methyl-5-trifluoromethyl-1H-pyrazole and diphenyliodonium chloride as starting materials, the course of the reaction in the process (b) according to the invention can be illustrated by the following equation:

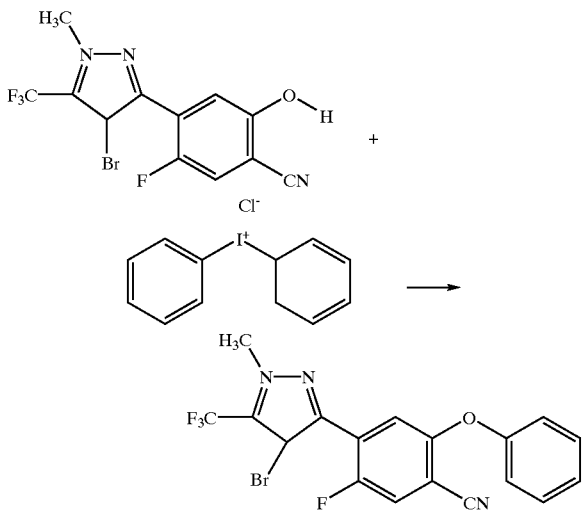

The formula (II) provides a general definition of the 3-halogenophenyl-pyrazoles to be used as starting materials in the process (a) according to the invention for preparing compounds of the general formula (I). In the general formula (II), $R^1$, $R^2$, $R^3$ and $R^4$ each preferably have those meanings which have already been mentioned above, in connection with the description of the compounds of the general formula (I) according to the invention, as being preferred or as being particularly preferred for $R^1$, $R^2$, $R^3$ and $R^4$.

The starting materials of the general formula (II) are known and/or can be prepared by processes which are known per se (cf. WO-A-97/40018, WO-A-97/46535).

The formula (III) provides a general definition of the aryl compounds further to be used as starting materials in the process (a) according to the invention. In the general formula (III), n, Q and X each preferably have those meanings which have already been mentioned above, in connection with the description of the compounds of the general formula (I) according to the invention, as being preferred or as being particularly preferred for n, Q and X.

Suitable metal salts of compounds of the formula (III) are preferably the alkali metal or alkaline earth metal salts, in particular the sodium and potassium salts.

The starting materials of the general formula (III) are known organic chemicals for synthesis.

The formula (IV) provides a general definition of the substituted 3-phenyl-pyrazoles to be used as starting materials in the process (b) according to the invention for preparing compounds of the general formula (I). In the general formula (IV), Q, $R^1$, $R^2$, $R^3$ and $R^4$ each preferably have those meanings which have already been mentioned above, in connection with the description of the compounds of the general formula (I) according to the invention, as being preferred or as being particularly preferred for Q, $R^1$, $R^2$, $R^3$ and $R^4$.

Starting materials of the general formula (IV) are known and/or can be prepared by processes which are known per se (cf. WO-A-97/40018, WO-A-97/46535).

Suitable metal salts of compounds of the formula (IV) are preferably the alkali metal or alkaline earth metal salts, in particular the sodium and potassium salts.

The formula (V) provides a general definition of the diaryliodonium compounds further to be used as starting materials in the process (b) according to the invention. In the general formula (V), n and X each preferably have those meanings which have already been mentioned above, in connection with the description of the compounds of the general formula (I) according to the invention, as being preferred or as being particularly preferred for n and X.

The starting materials of the general formula (V) are known and/or can be prepared by processes which are known per se (cf. J. Chem. Soc. Perkin Trans. I 1987, 241–249).

The processes according to the invention for preparing the compounds of the general formula (I) are preferably carried out using diluents. Suitable diluents for carrying out the processes (a) and (b) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes (a) and (b) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethyl-amino-pyridine, N-methyl-piperidine, 1,4-diazabicyclo[2,2,2]octane (DABCO), 1,5-diazabicyclo[4,3,0]-non-5-ene (DBN), or 1,8-diazabicyclo[5,4,0]-undec-7-ene (DBU).

Other suitable reaction auxiliaries for the processes (a) and (b) according to the invention are phase-transfer catalysts. Examples of such catalysts which may be mentioned are:

tetrabutylammonium bromide, tetrabutylammonium chloride, tetraoctylammonium chloride, tetrabutylammonium hydrogensulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

When carrying out the processes (a) and (b) according to the invention, the reaction temperatures can be varied within a relatively wide range. In general, the reaction is carried out at temperatures between 0° C. and 150° C., preferably between 10° C. and 120° C.

The processes according to the invention are generally carried out under atmospheric pressure. However, it is also possible to carry out the processes according to the invention under elevated or reduced pressure—in general between 0.1 bar and 10 bar.

For carrying out the process according to the invention, the starting materials are generally employed in approximately equimolar amounts. However, it is also possible to employ a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

The active compounds according to the invention can be used as defoliants, desiccants, haulm killers and, especially, as weed killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crop plants of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crop plants of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The active compounds according to the invention are suitable, depending on the concentration, for the total control of weeds, for example on industrial terrain and railway tracks, and on paths and squares with or without tree plantings. Likewise, the active compounds according to the invention can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, sports fields and pastureland, and for the selective control of weeds in annual cultures.

The compounds of the general formula (I) according to the invention have strong herbicidal activity and a broad spectrum of activity when applied to the soil and to the above-ground parts of plants. To a certain extend they are also suitable for the selective control of monocotyledonous and dicotyledonous weeds in monocotyledonous and dicotyledonous crops, both pre-emergence and post-emergence.

To a certain extend, the compounds of the general formula (I) also have fingicidal activity, in particular against mildew.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ, for example, organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example, ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-forming agents are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example, lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, such as or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, ciforidazon, chlorimuron(-ethyl), chlornitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, etharnetsulfuiron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuiron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

(Process (a))

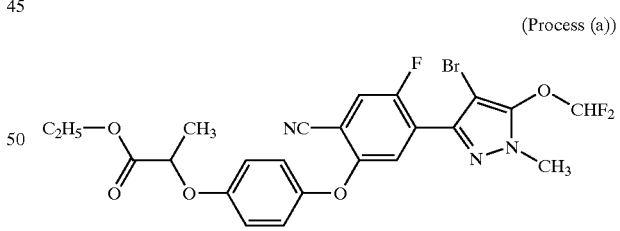

Under argon as protective gas, 0.24 g (6.0 mmol) of sodium hydride (60%) in mineral oil is added to a solution of 1.05 g (5.0 mmol) of ethyl 2-(4-hydroxy-phenoxy)-propionate in 25 ml of dimethyl sulphoxide. The mixture is stirred at room temperature (approximately 20° C.) for 15 minutes and then admixed with 1.8 g (5.0 mmol) of 4-bromo-3-(4-cyano-2,5-difluoro-phenyl)-5-difluoromethoxy-1-methyl-1H-pyrazole. The mixture is stirred at 50° C. for 2.5 hours and admixed with water and dichloromethane and acidified with hydrochloric acid, and the organic phase is separated off. The organic phase is washed successively with saturated sodium bicarbonate solution and sodium chloride solution, dried over magnesium sulphate and freed from the solvent under reduced pressure. The resulting crude product is purified by column chromatography using dichloromethane as the mobile phase.

This gives 1.8 g (56% of theory) of ethyl 2-[4-[2-cyano-5-[4-bromo-5-(difluoromethoxy)-1-methyl-1H-pyrazo-3-yl]-4-fluoro-phenoxy]-phenoxy]-propionate of melting point 60° C.

Example 2

(Process (b))

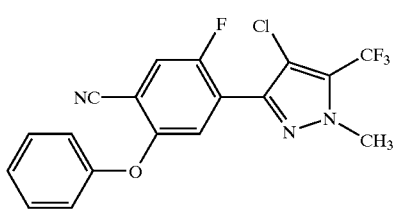

0.4 g (2.9 mmol) of potassium carbonate and 0.6 g (1.9 mmol) of diphenyliodonium chloride are added successively to a solution of 0.6 g (1.88 mmol) of 4-chloro-3-(4-cyano-2-fluoro-5-hydroxy-phenyl)-1-methyl-5-trifluoromethyl-1H-pyrazole in 10 ml of acetonitrile. The mixture is stirred at reflux temperature for one hour, most of the solvent is then removed, and the residue is admixed with 50 ml of water, acidified with 2N hydrochloric acid and extracted with ethyl acetate. The organic phase is washed successively with saturated sodium bicarbonate solution and sodium chloride solution, dried over magnesium sulphate freed from the solvent under reduced pressure and stirred with diisopropyl ether.

This gives 0.5 g (67% of theory) of 4-chloro-3-(4-cyano-2-fluoro-5-phenoxyphenyl)-1-methyl-5-trifluoromethyl-1H-pyrazole of m.p. 123° C.

Similarly to Examples 1 and 2, and in accordance with the general description of the preparation process according to the invention, it is also possible to prepare, for example, the compounds of the general formula (I) listed in Table 1 below.

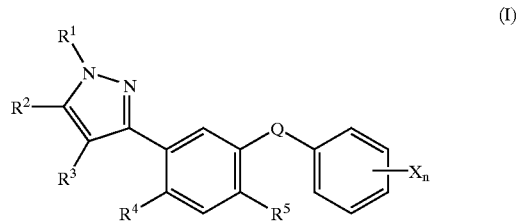

(I)

TABLE 1

Examples of compounds of the formula (I)

| Ex. No. | Q | $R^1$ | $R^2$ | $R^3$ | $R^4$ | $R^5$ | (Position) $X_n$ | | Physical Data |
|---|---|---|---|---|---|---|---|---|---|
| 3 | O | $CH_3$ | $CF_3$ | Cl | F | CN | (4) | $CH_3$, $C_2H_5$, O, O, O | m.p.: 86° C. |
| 4 | O | $CH_3$ | $OCHF_2$ | H | F | CN | (4) | $CH_3$, $C_2H_5$, O, O, O | m.p.: 80° C. |
| 5 | O | $CH_3$ | $SO_2CH_3$ | Br | F | CN | (4) | $CH_3$, $C_2H_5$, O, O, O | m.p.: 102° C. |
| 6 | O | $CH_3$ | $OCHF_2$ | Cl | F | CN | (4) | $CH_3$, $C_2H_5$, O, O, O | (amorphous) |
| 7 | O | $CH_3$ | $CF_3$ | Cl | F | CN | (4) | $CH_3$, $CH_3$, O, NH, O | m.p.: 175° C. |

TABLE 1-continued

Examples of compounds of the formula (I)

| Ex. No. | Q | R¹ | R² | R³ | R⁴ | R⁵ | (Position) $X_n$ | Structure | Physical Data |
|---|---|---|---|---|---|---|---|---|---|
| 8 | O | CH₃ | OCHF₂ | Br | F | CN | (4) | CH₃O–CH(CH₃)–C(=O)–NH–CH₃ | m.p.: 149° C. |
| 9 | O | CH₃ | SO₂CH₃ | Br | F | CN | (4) | CH₃O–CH(CH₃)–C(=O)–NH–CH₃ | m.p.: 152° C. |
| 10 | O | CH₃ | OCHF₂ | Cl | F | CN | (4) | CH₃O–CH(CH₃)–C(=O)–NH–CH₃ | m.p.: 160° C. |
| 11 | O | CH₃ | OCHF₂ | Cl | F | CN | — | | m.p.: 110° C. |
| 12 | O | CH₃ | OCHF₂ | Cl | F | CN | (4) | CH=CH–C(=O)–OC₂H₅ | log.P = 5.16[a] |
| 13 | O | CH₃ | OCHF₂ | Cl | F | CN | (4) | CH₂–CH₂–C(=O)–OC₂H₅ | log.P = 4.26[a] |
| 14 | O | CH₃ | OCHF₂ | Cl | F | CN | (3) | CH=CH–C(=O)–OC₂H₅ | log.P = 4.30[a] |
| 15 | O | CH₃ | OCHF₂ | Cl | F | CN | (3) | CH₂–CH₂–C(=O)–OC₂H₅ | log.P = 4.26[a] |
| 16 | O | CH₃ | OCHF₂ | Cl | F | CN | (4) | CH₃O–CH₂–C(=O)–OC₂H₅ | log.P = 3.87[a] |
| 17 | O | CH₃ | OCHF₂ | Br | F | CN | (4) | CH₃O–CH₂–C(=O)–OC₂H₅ | log.P = 3.87[a] |
| 18 | O | CH₃ | OCHF₂ | Br | F | CN | (3) | CH₂–CH₂–C(=O)–OC₂H₅ | ¹H-NMR (CDCl₃, δ): 2.60–2.65, 2.93–2.98, 3.82, 4.08–4.15, 7.45–7.48 ppm |
| 19 | O | CH₃ | OCHF₂ | Cl | F | CN | (4) | CH₃–CH₂–C(=O)–OCH₃ | ¹H-NMR (CDCl₃, δ): 3.57, 3.64, 3.73, 7.38–7.41 ppm |
| 20 | O | CH₃ | OCHF₂ | Cl | F | CN | (4) | CH₃O–CH₂–C(=O)–OCH₃ | ¹H-NMR (CDCl₃, δ): 3.80, 3.82, 4.65, 6.67, 7.43–7.46 ppm |

TABLE 1-continued

Examples of compounds of the formula (I)

| Ex. No. | Q | $R^1$ | $R^2$ | $R^3$ | $R^4$ | $R^5$ | (Position) $X_n$ | Physical Data |
|---|---|---|---|---|---|---|---|---|
| 21 | O | $CH_3$ | $OCHF_2$ | Cl | F | CN | (4) $COOC_2H_5$ | logP = 4.19[a)] |
| 22 | O | $CH_3$ | $OCHF_2$ | Cl | F | CN | (2) $COOC_2H_5$ | $^1$H-NMR (CDCl$_3$, δ): 3.78, 4.22–4.29, 6.65, 8.04–8.07 ppm |
| 23 | O | $CH_3$ | $OCHF_2$ | Cl | F | CN | (3) OH | m.p.: 139° C. |
| 24 | O | $CH_3$ | $OCHF_2$ | Cl | F | CN | (3) [CH$_3$, C$_2$H$_5$ structure] | $^1$H-NMR (CDCl$_3$, δ): 1.48–1.50, 3.78, 4.06–4.13, 4.99–5.04, 8.12–8.16 ppm |
| 25 | O | $CH_3$ | $OCHF_2$ | Cl | F | CN | (2) $COOCH_3$ | |
| 26 | O | $CH_3$ | $OCHF_2$ | Cl | F | CN | (3) $COOCH_3$ | |
| 27 | O | $CH_3$ | $OCHF_2$ | Cl | F | CN | (4) $COOCH_3$ | |
| 28 | O | $CH_3$ | $OCHF_2$ | Cl | F | CN | (3) $COOC_2H_5$ | |
| 29 | O | $CH_3$ | $OCHF_2$ | Cl | F | CN | (2) $COOC_3H_7$-i | |
| 30 | O | $CH_3$ | $OCHF_2$ | Cl | F | CN | (3) $COOC_3H_7$-i | |
| 31 | O | $CH_3$ | $OCHF_2$ | Cl | F | CN | (4) $COOC_3H_7$-i | |
| 32 | O | $CH_3$ | $CF_3$ | Cl | F | CN | (2) $COOCH_3$ | |
| 33 | O | $CH_3$ | $CF_3$ | Cl | F | CN | (3) $COOCH_3$ | |
| 34 | O | $CH_3$ | $CF_3$ | Cl | F | CN | (4) $COOCH_3$ | |
| 35 | O | $CH_3$ | $CF_3$ | Cl | F | CN | (3) $COOC_2H_5$ | |
| 36 | O | $CH_3$ | $CF_3$ | Cl | F | CN | (2) $COOC_3H_7$-i | |
| 37 | O | $CH_3$ | $CF_3$ | Cl | F | CN | (3) $COOC_3H_7$-i | |
| 38 | O | $CH_3$ | $CF_3$ | Cl | F | CN | (4) $COOC_3H_7$-i | |
| 39 | O | $CH_3$ | $CF_3$ | Cl | F | CN | (2) $COOC_2H_5$ | |
| 40 | O | $CH_3$ | $CF_3$ | Cl | F | CN | (4) $COOC_2H_5$ | |
| 41 | O | $CH_3$ | $CF_3$ | Cl | F | CN | (2) $CF_3$ | |
| 42 | O | $CH_3$ | $CF_3$ | Cl | F | CN | (3) $CF_3$ | |
| 43 | O | $CH_3$ | $CF_3$ | Cl | F | CN | (4) $CF_3$ | |
| 44 | O | $CH_3$ | $CF_3$ | Cl | F | CN | (2) $NO_2$ | |
| 45 | O | $CH_3$ | $CF_3$ | Cl | F | CN | (3) $NO_2$ | |
| 46 | O | $CH_3$ | $CF_3$ | Cl | F | CN | (4) $NO_2$ | |
| 47 | O | $CH_3$ | $CF_3$ | Cl | F | CN | (2) $CH_3$ | |
| 48 | O | $CH_3$ | $CF_3$ | Cl | F | CN | (3) $CH_3$ | |
| 49 | O | $CH_3$ | $CF_3$ | Cl | F | CN | (4) $CH_3$ | |
| 50 | O | $CH_3$ | $OCHF_2$ | Cl | F | CN | (2) $CF_3$ | logP: 4.36[a)] |
| 51 | O | $CH_3$ | $OCHF_2$ | Cl | F | CN | (3) $CF_3$ | logP: 4.55[a)] |
| 52 | O | $CH_3$ | $OCHF_2$ | Cl | F | CN | (4) $CF_3$ | logP: 4.59[a)] |
| 53 | O | $CH_3$ | $OCHF_2$ | Cl | F | CN | (2) $NO_2$ | |
| 54 | O | $CH_3$ | $OCHF_2$ | Cl | F | CN | (3) $NO_2$ | |
| 55 | O | $CH_3$ | $OCHF_2$ | Cl | F | CN | (4) $NO_2$ | |
| 56 | O | $CH_3$ | $OCHF_2$ | Cl | F | CN | (2) $CH_3$ | logP: 4.40[a)] |
| 57 | O | $CH_3$ | $OCHF_2$ | Cl | F | CN | (3) $CH_3$ | logP: 4.43[a)] |
| 58 | O | $CH_3$ | $OCHF_2$ | Cl | F | CN | (4) $CH_3$ | logP: 4.45[a)] |
| 59 | O | $CH_3$ | $OCHF_2$ | Cl | F | CN | (2) $OCH_3$ | logP: 3.98[a)] |
| 60 | O | $CH_3$ | $OCHF_2$ | Cl | F | CN | (3) $OCH_3$ | logP: 4.13[a)] |
| 61 | O | $CH_3$ | $OCHF_2$ | Cl | F | CN | (4) $OCH_3$ | logP: 4.05[a)] |
| 62 | O | $CH_3$ | $OCHF_2$ | Cl | F | CN | (2) $SCH_3$ | |
| 63 | O | $CH_3$ | $OCHF_2$ | Cl | F | CN | (4) $SCH_3$ | |
| 64 | O | $CH_3$ | $OCHF_2$ | Cl | F | CN | (2) CN | |
| 65 | O | $CH_3$ | $OCHF_2$ | Cl | F | CN | (3) CN | |
| 66 | O | $CH_3$ | $OCHF_2$ | Cl | F | CN | (4) CN | |
| 67 | O | $CH_3$ | $OCHF_2$ | Cl | F | CN | (2) Cl | logP: 4.28[a)] |
| 68 | O | $CH_3$ | $OCHF_2$ | Cl | F | CN | (3) Cl | logP: 4.49[a)] |
| 69 | O | $CH_3$ | $OCHF_2$ | Cl | F | CN | (4) Cl | logP: 4.49[a)] |
| 70 | O | $CH_3$ | $OCHF_2$ | Cl | F | CN | (2) F | logP: 4.02[a)] |
| 71 | O | $CH_3$ | $OCHF_2$ | Cl | F | CN | (3) F | logP: 4.17[a)] |
| 72 | O | $CH_3$ | $OCHF_2$ | Cl | F | CN | (4) F | logP: 4.13[a)] |
| 73 | O | $CH_3$ | $OCHF_2$ | Cl | F | CN | (3) $N(CH_3)_2$ | |
| 74 | O | $CH_3$ | $OCHF_2$ | Cl | F | CN | (2) $OCHF_2$ | |
| 75 | O | $CH_3$ | $OCHF_2$ | Cl | F | CN | (2) $OCF_3$ | |
| 76 | O | $CH_3$ | $OCHF_2$ | Cl | F | CN | (4) $OCF_3$ | logP: 4.70[a)] |
| 77 | O | $CH_3$ | $CF_3$ | Cl | F | CN | (4) $OCF_3$ | |
| 78 | O | $CH_3$ | $CF_3$ | Cl | F | CN | (2) $OCHF_2$ | |
| 79 | O | $CH_3$ | $CF_3$ | Cl | F | CN | (4) $SO_2N(CH_3)_2$ | |
| 80 | O | $CH_3$ | $OCHF_2$ | Cl | F | CN | (4) $SO_2N(CH_3)_2$ | |
| 81 | O | $CH_3$ | $CF_3$ | Cl | F | CN | (4) $CON(CH_3)_2$ | |
| 82 | O | $CH_3$ | $OCHF_2$ | Cl | F | CN | (4) $CON(CH_3)_2$ | |
| 83 | O | $CH_3$ | $CF_3$ | Cl | F | CN | (4) $COCH_3$ | |
| 84 | O | $CH_3$ | $OCHF_2$ | Cl | F | CN | (4) $COCH_3$ | logP: 3.66[a)] |

TABLE 1-continued

Examples of compounds of the formula (I)

| Ex. No. | Q | R¹ | R² | R³ | R⁴ | R⁵ | (Position) $X_n$ | Physical Data |
|---|---|---|---|---|---|---|---|---|
| 85 | O | CH₃ | OCHF₂ | Br | F | CN | (4) Cl | m.p.: 135° C. |
| 86 | O | CH₃ | OCHF₂ | Br | F | CN | (3) Cl | m.p.: 127° C. |
| 87 | O | CH₃ | OCHF₂ | Br | F | CN | (2) Cl | m.p.: 101° C. |
| 88 | O | CH₃ | OCHF₂ | Br | F | CN | (4) F | m.p.: 97° C. |
| 89 | O | CH₃ | OCHF₂ | Br | F | CN | (3) F | m.p: 102° C. |
| 90 | O | CH₃ | OCHF₂ | Br | F | CN | (2) F | m.p.: 107° C. |
| 91 | O | CH₃ | OCHF₂ | Br | F | CN | (5) OCH₃ | m.p.: 127° C. |
| 92 | O | CH₃ | OCHF₂ | Br | F | CN | (3) OCH₃ | m.p.: 98° C. |
| 93 | O | CH₃ | OCHF₂ | Br | F | CN | (2) OCH₃ | m.p.: 127° C. |
| 94 | O | CH₃ | OCHF₂ | Br | F | CN | (2) CH₃ | m.p.: 116° C. |
| 95 | O | CH₃ | OCHF₂ | Br | F | CN | (3) CH₃ | m.p.: 147° C. |
| 96 | O | CH₃ | OCHF₂ | Br | F | CN | (4) CH₃ | m.p.: 122° C. |
| 97 | O | CH₃ | OCHF₂ | Br | F | CN | (4) COCH₃ | m.p.: 157° C. |
| 98 | O | CH₃ | OCHF₂ | Br | F | CN | (3) NHSO₂C₂H₅ | m.p.: resin |
| 99 | O | CH₃ | OCHF₂ | Br | F | CN | (4) CF₃ | m.p.: resin |
| 100 | O | CH₃ | OCHF₂ | Br | F | CN | (3) CF₃ | m.p.: 88° C. |
| 101 | O | CH₃ | OCHF₂ | Br | F | CN | (2) CF₃ | m.p.: 130° C. |
| 102 | O | CH₃ | OCHF₂ | Br | F | CN | (2) CON(CH₃)₂ | m.p.: 128° C. |
| 103 | O | CH₃ | OCHF₂ | Br | F | CN | (3) N(CH₃)₂ | m.p.: resin |
| 104 | O | CH₃ | OCHF₂ | Br | F | CN | (2,3) F₂ | m.p.: 100° C. |
| 105 | O | CH₃ | OCHF₂ | Br | F | CN | (3,4) Cl₂ | m.p.: 101° C. |
| 106 | O | CH₃ | OCHF₂ | Br | F | CN | (2) OCH(CH₃)₂ | m.p.: resin |
| 107 | O | CH₃ | OCHF₂ | Br | F | CN | (3,4) (CH₃)₂ | m.p.: 115° C. |
| 108 | O | CH₃ | OCHF₂ | Br | F | CN | (4) OCF₃ | m.p.: 100° C. |
| 109 | O | CH₃ | OCHF₂ | Br | F | CN | (3) OCF₃ | m.p.: oil |
| 110 | O | CH₃ | OCHF₂ | Br | F | CN | (3) N(C₂H₅)₂ | m.p.: resin |
| 111 | O | CH₃ | OCHF₂ | Br | F | CN | (3) CN | m.p.: 125° C. |
| 112 | O | CH₃ | OCHF₂ | Br | F | CN | (2,3) (OCH₃)₂ | logP: 3.80ᵃ⁾ |
| 113 | O | CH₃ | OCHF₂ | Br | F | CN | (2) Cl, (5) CH₃ | m.p.: resin |
| 114 | O | CH₃ | OCHF₂ | Br | F | CN | (3,4) (OCH₃)₂ | m.p.: 118° C. |
| 115 | O | CH₃ | OCHF₂ | Cl | F | CN | (2) CON(CH₃)₂ | logP: 3.20ᵃ⁾ |
| 116 | O | CH₃ | OCHF₂ | Cl | F | CN | (3) N(CH₃)₂ | logP: 4.38ᵃ⁾ |
| 117 | O | CH₃ | OCHF₂ | Cl | F | CN | (2,3) F₂ | logP: 4.13ᵃ⁾ |
| 118 | O | CH₃ | OCHF₂ | Cl | F | CN | (3,4) Cl₂ | logP: 4.89ᵃ⁾ |
| 119 | O | CH₃ | OCHF₂ | Cl | F | CN | (2) OCH(CH₃)₂ | logP: 4.55ᵃ⁾ |
| 120 | O | CH₃ | OCHF₂ | Cl | F | CN | (3,4) (CH₃)₂ | logP: 4.74ᵃ⁾ |
| 121 | O | CH₃ | OCHF₂ | Cl | F | CN | (2) CH₂N(CH₃)₂ | logP: 2.03ᵃ⁾ |
| 122 | O | CH₃ | OCHF₂ | Cl | F | CN | (3) N(C₂H₅)₂ | logP: 4.40ᵃ⁾ |
| 123 | O | CH₃ | OCHF₂ | Cl | F | CN | (3) OCF₃ | logP: 4.72ᵃ⁾ |
| 124 | O | CH₃ | OCHF₂ | Cl | F | CN | (2,3) (OCH₃)₂ | logP: 3.98ᵃ⁾ |
| 125 | O | CH₃ | OCHF₂ | Cl | F | CN | (2) Cl, (5) CH₃ | logP: 4.59ᵃ⁾ |
| 126 | O | CH₃ | OCHF₂ | Cl | F | CN | (3,4) (OCH₃)₂ | logP: 3.72ᵃ⁾ |

The log P values given in Table 1 were determined in accordance with the EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data are labelled a) in Table 1.

(b) Mobile phases for the determination in the neutral range: 0.01 molar aqueous phosphate buffer solution, acetonitrile; linear gradient from 10% acetonitrile to 90% acetonitrile—the corresponding data are labelled b) in Table 1.

The calibration was carried out using unbranched alkan-2-ones (having from 3 to 16 carbon atoms) whose log P values are known (determination of the log P values by the retention times by linear interpolation between two successive alkanones).

The lambda max values were determined by using the UV spectra from 200 nm to 400 nm in the maxima of the chromatographic signals.

Starting Materials of the Formula (III)

Example (III-1)

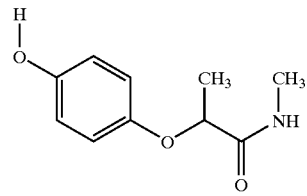

A suspension of 20 g (95 mmol) of ethyl 2-(4-hydroxy-phenoxy)-propionate in 120 ml of 30% strength aqueous methylamine solution was heated to 70° C. for 7 hours. After cooling, the mixture is discharged onto a mixture of ice/hydrochloric acid and extracted with dichloromethane. The organic phase is separated off and washed successively with saturated sodium bicarbonate solution and sodium chloride solution, dried over magnesium sulphate and freed from the solvent under reduced pressure.

This gives 14.1 g (76% of theory) of N-methyl-2-(4-hydroxy-phenoxy)-propionamide of melting point 112° C.

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After approximately 24 hours, the soil is sprayed with the preparation of the active compound in such a way as to apply the particular amount of active compound desired per unit area. The concentration of the spray liquor is chosen so that the amount of active compound desired in each case is applied in 1000 liter of water per hectare.

After three weeks, the degree of damage to the plants is rated in % damage in comparison with the development of the untreated control.

The figures denote:

0% = no effect (like untreated control)
100% = total destruction

In this test, for example the compounds of Preparation Example 1, 8 and 10 show strong activity against weeds, combined with good compatibility with crop plants, such as, for example, barley, wheat, maize and soya.

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the amounts of active compound desired in each case are applied in 1000 l of water/ha.

After three weeks, the degree of damage to the plants is rated in % damage in comparison with the development of the untreated control.

The figures denote:

0%=no effect (like untreated control)
100%=total destruction

In this test, for example the compounds of Preparation Example 1, 3, 5, 6, 7, 8, 9 show strong activity against weeds.

What is claimed is:

1. A substituted 3-aryl-pyrazole of the formula (I)

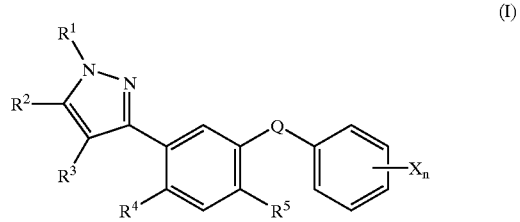

wherein n represents the number 1,

Q represents O (oxygen), $R^1$ represents hydrogen or represents unsubstituted alkyl having 1 to 6 carbon atoms, $R^2$ represents halogen-substituted alkyl having 1 to 6 carbon atoms, $R^3$ represents halogen or unsubstituted or cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl having 1 to 6 carbon atoms, $R^4$ represents hydrogen or halogen, $R^5$ represents cyano, and X represents $C_1$–$C_4$-alkoxy-carbonyl- or $C_1$–$C_4$-alkylamino-carbonyl-substituted alkoxy having in each case 1 to 6 carbon atoms.

2. A substituted 3-aryl-pyrazole according to claim 1, wherein n represents the number 1, Q represents O (oxygen), $R^1$ represents hydrogen or represents methyl, ethyl, n- or i-propyl, n-, i-, s- or t-butyl, $R^2$ represents fluorine- and/or chlorine-substituted methyl, ethyl, n- or i-propyl, n-, i-, s- or t-butyl, $R^3$ represents fluorine, chlorine, bromine, or represents in each case unsubstituted or cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulfonyl-, n- or i-propylsulphonyl-substituted methyl, ethyl, n- or i-propyl, $R^4$ represents hydrogen or fluorine, chlorine or bromine, $R^5$ represents cyano, and X represents methoxycarbonyl-, ethoxycarbonyl- n- or i-propoxycarbonyl-, methylaminocarbonyl-, ethylaminocarbonyl-, n- or i-propylaminocarbonyl-, dimethylaminocarbonyl- or diethylaminocarbonyl-substituted methoxy, ethoxy, n- or i-propoxy, n-, i-, s- or t-butoxy.

3. A substituted 3-aryl-pyrazole according to claim 1, wherein n represents the number 1, Q represents O (oxygen), $R^1$ represents hydrogen or represents methyl or ethyl, $R^2$ represents fluorine- and/or chlorine-substituted methyl, ethyl, n- or i-propyl, n-, i-, s- or t-butyl, $R^3$ represents chlorine or bromine, $R^4$ represents hydrogen or fluorine or chlorine, $R^5$ represents cyano, and X represents methoxycarbonyl-, ethoxycarbonyl- n- or i-propoxycarbonyl-, methylaminocarbonyl-, ethylaminocarbonyl-, n- or i-propylaminocarbonyl-, dimethylaminocarbonyl- or diethylamino-carbonyl-substituted methoxy, ethoxy, n- or i-propoxy.

4. A substituted 3-aryl-pyrazole according to claim 1, having the formula (IA)

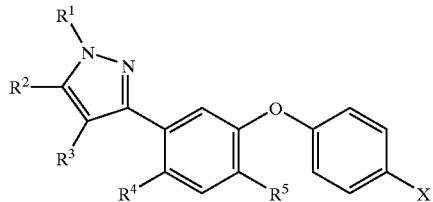

(IA)

wherein
- $R^1$ represents methyl,
- $R^2$ represents trifluromethyl,
- $R^3$ represents chlorine or bromine,
- $R^4$ represents hydrogen or fluorine or chlorine,
- $R^5$ represents cyano, and
- X represents methoxycarbonyl-, ethoxycarbonyl-, n- or i-propoxy-carbonyl-, methylaminocarbonyl-, ethylaminocarbonyl-, n- or i-propylamino-carbonyl-, dimethylaminocarbonyl- or diethylaminocarbonyl-substituted methoxy or ethoxy.

5. A substituted 3-aryl-pyrazole according to claim 1, having the formula (IB)

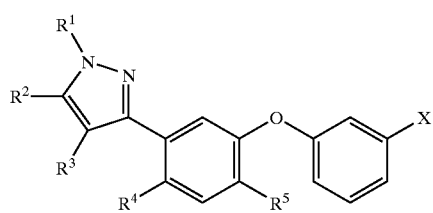

(IB)

wherein
- $R^1$ represents methyl,
- $R^2$ represents trifluoromethyl,
- $R^3$ represents chlorine or bromine,
- $R^4$ represents hydrogen or fluorine or chlorine,
- $R^5$ represents cyano, and
- X represents methoxycarbonyl-, ethoxycarbonyl-, n- or i-propoxy-carbonyl-, methylaminocarbonyl-, ethylaminocarbonyl-, n- or i-propylamino-carbonyl-, dimethylaminocarbonyl- or diethylaminocarbonyl-substituted methoxy or ethoxy.

6. A process for preparing substituted a 3-aryl-pyrazole according to claim 1, comprising reacting a 3-halogenophenyl-pyrazole of the formula (II)

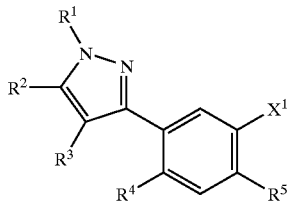

(II)

wherein
$R^1$, $R^2$, $R^3$, $R^4$ and $R^5$ are each as defined in claim 1 and $X^1$ represents halogen with an aryl compound of the formula (III)

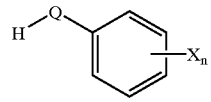

(III)

wherein
n, Q and X are each as defined in claim 1 or with a metal salt of a compound of the formula (III).

7. A process according to claim 6 comprising reacting a 3-halogenophenyl-pyrazole of the formula (II) with an aryl compound of the formula (III) in the presence of an ingredient selected from the group consisting of reaction auxiliaries, diluents and mixtures thereof.

8. A process for preparing a substituted 3-aryl-pyrazole according to claim 4, comprising reacting (a) a 3-halogenophenyl-pyrazole of the formula (II)

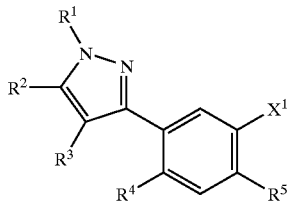

(II)

wherein $R^1$, $R^2$, $R^3$, $R^4$ and $R^5$ are each as defined in claim 4 and $X^1$ represents halogen with an aryl compound of the formula (IIIA)

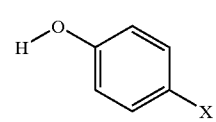

(IIIA)

wherein X is as defined in claim 4, or with a metal salt of a compound of the formula (IIIA) or (b) a substituted 3-phenyl-pyrazole of the formula (IVA)

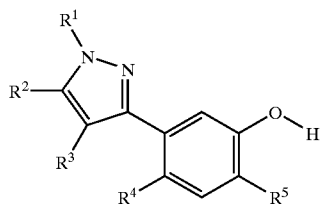

(IVA)

wherein $R^1$, $R^2$, $R^3$, $R^4$ and $R^5$ are each as defined in claim 4, or a metal salt of a compound of the formula (IVA)

with a diaryliodonium compound of the formula (VA)

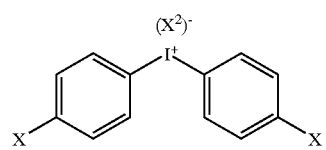

(VA)

wherein X is as defined in claim 4 and $X^2$ represents halogen.

9. A process for preparing substituted 3-aryl-pyrazoles according to claim 5, comprising reacting (a) a 3-halogenophenyl-pyrazole of the formula (II)

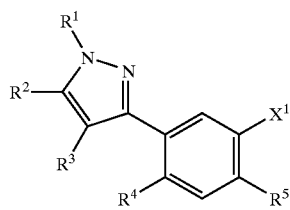

(II)

wherein $R^1$, $R^2$, $R^3$, $R^4$ and $R^5$ are each as defined in claim 5 and $X^1$ represents halogen with an aryl compound of the formula (IIIB)

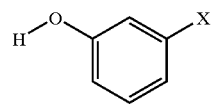

(IIIB)

wherein X is as defined in claim 5, or with a metal salt of a compound of the formula (IIIB) or (b) a substituted 3-phenyl-pyrazole of the formula (IVB)

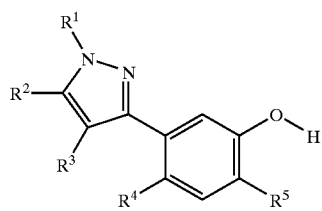

(IVB)

wherein $R^1$, $R^2$, $R^3$, $R^4$ and $R^5$ are each as defined in claim 5, or a metal salt of a compound of the formula (IVB)

with a diaryliodonium compound of the formula (VB)

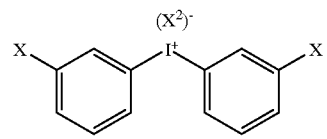

(VB)

wherein X is as defined in claim 5 and $X^2$ represents halogen.

10. A method for controlling undesirable plants, comprising the step of applying one or more 3-aryl-pyrazole compounds according to claim 1 to undesirable plants and/or their habitat.

11. A method of controlling fungi, comprising the step of applying one or more 3-aryl-pyrazole compounds according to claim 1 to fungi and/or their habitat.

12. A composition for the treatment of plants, comprising one or more 3-aryl-pyrazole compounds according to claim 1 and one or more extenders.

13. A composition for the treatment of plants, comprising one or more 3-aryl-pyrazole according to claim 2 and one or more extenders.

14. A composition for the treatment of plants, comprising one or more 3-aryl-pyrazole according to claim 3 and one or more extenders.

15. A composition for the treatment of plants, comprising one or more 3-aryl-pyrazole compounds according to claim 4 and one or more extenders.

16. A composition for the treatment of plants, comprising one or more 3-aryl-pyrazole compounds according to claim 5 and one or more extenders.

17. A method for controlling undesirable plants and/or fungi, comprising the step of applying one or more 3-aryl-pyrazole compounds according to claim 4 to undesirable plants, fungi and/or their habitat.

18. A method for controlling undesirable plants and/or fungi, comprising the step of applying one or more 3-aryl-pyrazole according to claim 5 to undesirable plants, fungi and/or their habitat.

* * * * *